(12) United States Patent
Bürger et al.

(10) Patent No.: US 9,804,134 B2
(45) Date of Patent: Oct. 31, 2017

(54) CONNECTOR UNIT AND CONNECTING SYSTEM FOR CONNECTING CAPILLARIES, IN PARTICULAR FOR HIGH-PERFORMANCE LIQUID CHROMATOGRAPHY

(75) Inventors: Daniel Bürger, Raisting (DE); Michael Schadl, Schiltberg (DE)

(73) Assignee: DIONEX SOFTRON GMBH, Germering (DE)

( * ) Notice: Subject to any disclaimer, the term of this patent is extended or adjusted under 35 U.S.C. 154(b) by 785 days.

(21) Appl. No.: 14/115,143

(22) PCT Filed: Apr. 25, 2012

(86) PCT No.: PCT/DE2012/100115
§ 371 (c)(1),
(2), (4) Date: Nov. 1, 2013

(87) PCT Pub. No.: WO2012/149930
PCT Pub. Date: Nov. 8, 2012

(65) Prior Publication Data
US 2014/0145437 A1    May 29, 2014

(30) Foreign Application Priority Data
May 2, 2011    (DE) .................. 10 2011 050 037

(51) Int. Cl.
*F16L 21/02* (2006.01)
*G01N 30/60* (2006.01)

(52) U.S. Cl.
CPC ......... *G01N 30/60* (2013.01); *G01N 30/6004* (2013.01); *G01N 30/6026* (2013.01); *G01N 30/6039* (2013.01)

(58) Field of Classification Search
CPC .............. G01N 30/60; G01N 30/6026; G01N 30/6039; G01N 30/6004
USPC ........................................... 285/342
See application file for complete search history.

(56) References Cited

U.S. PATENT DOCUMENTS

| | | | |
|---|---|---|---|
| 2,077,035 A | | 4/1937 | Bredeson et al. |
| 2,470,546 A | * | 5/1949 | Carlson .................. F16L 19/12 285/250 |
| 3,880,452 A | | 4/1975 | Fields |
| 4,083,702 A | * | 4/1978 | Hartigan ............ G01N 30/6039 96/106 |
| 4,281,679 A | * | 8/1981 | Stearns .................. F16K 15/04 137/515.5 |
| 4,619,473 A | | 10/1986 | Someya |

(Continued)

FOREIGN PATENT DOCUMENTS

| | | |
|---|---|---|
| DE | 102009022368 B3 | 11/2010 |
| WO | 9745666 A1 | 12/1997 |

(Continued)

*Primary Examiner* — Brian Glessner
*Assistant Examiner* — Joshua Ihezie
(74) *Attorney, Agent, or Firm* — Timothy J. Ohara

(57) ABSTRACT

The invention relates to a connector unit for connecting capillaries, in particular for high-performance liquid chromatography, wherein a sealing element sealing the capillary protrudes at least partially into the interior of the capillary, while a portion of the sealing element that protrudes axially from the capillary can be subjected to a compressive force that is introduced via the capillary to obtain an axial or radial plastic and/or elastic deformation.

21 Claims, 7 Drawing Sheets

(56) References Cited

U.S. PATENT DOCUMENTS

| | | | | |
|---|---|---|---|---|
| 4,690,437 A | * | 9/1987 | Anderson, Jr. | G01N 30/6026 285/339 |
| 4,776,618 A | * | 10/1988 | Barree | F16L 19/07 285/341 |
| 5,163,722 A | * | 11/1992 | Worden | F16L 37/242 285/101 |
| 5,669,637 A | * | 9/1997 | Chitty | F16L 33/224 285/342 |
| 5,709,413 A | * | 1/1998 | Salyers | F16L 33/223 285/219 |
| 6,102,449 A | * | 8/2000 | Welsh | F16L 19/07 285/332 |
| 6,494,500 B1 | * | 12/2002 | Todosiev | G01N 30/6026 285/279 |
| 6,926,313 B1 | * | 8/2005 | Renzi | B01J 19/0093 285/342 |
| 7,909,367 B2 | * | 3/2011 | Plant | G01N 30/6004 285/249 |
| 8,006,367 B1 | * | 8/2011 | Best | B01L 3/563 29/516 |
| 8,702,130 B1 | * | 4/2014 | Zelechonok | G01N 30/6026 285/342 |
| 8,740,261 B2 | * | 6/2014 | Ford | G01N 30/6039 285/342 |
| 9,091,693 B2 | * | 7/2015 | Hochgraeber | G01N 30/6026 |
| 9,134,283 B2 | * | 9/2015 | Hochgraeber | G01N 30/6026 |
| 2010/0156089 A1 | * | 6/2010 | Zelechonok | G01N 30/6039 285/24 |
| 2010/0224543 A1 | | 9/2010 | Ellis et al. | |
| 2011/0025047 A1 | * | 2/2011 | Zelechonok | F16L 37/138 285/212 |
| 2011/0107823 A1 | * | 5/2011 | Dehmer | F16L 19/061 73/64.56 |
| 2011/0303593 A1 | * | 12/2011 | Reinhardt | F16L 19/061 210/143 |
| 2012/0061955 A1 | * | 3/2012 | Hochgraeber | G01N 30/6026 285/342 |
| 2013/0298647 A1 | * | 11/2013 | Falk-Jordan | F16L 19/061 73/61.55 |
| 2014/0130580 A1 | * | 5/2014 | McAdams | G01N 30/00 73/61.52 |

FOREIGN PATENT DOCUMENTS

| | | |
|---|---|---|
| WO | 2006091952 A1 | 8/2006 |
| WO | 2010133192 A1 | 11/2010 |

* cited by examiner

CONNECTOR UNIT AND CONNECTING SYSTEM FOR CONNECTING CAPILLARIES, IN PARTICULAR FOR HIGH-PERFORMANCE LIQUID CHROMATOGRAPHY

FIELD OF THE INVENTION

The invention relates to a connector unit for connecting capillaries, in particular for high-performance liquid chromatography (HPLC). Furthermore, the invention relates to a connecting system composed of a bushing unit and of a connector unit of said type.

BACKGROUND

In chromatography systems, liquids or gases are conveyed through suitable connecting lines between the components of the respective system. Said connecting lines which may be composed for example of high-grade steel have, at their ends, suitable connecting systems, also known as fittings, in order to be able to produce a sealed connection to the ports of the components.

A connecting system of said type was described as early as in the year 1975 in U.S. Pat. No. 3,880,452. Here, a capillary which forms the connecting line between two components is inserted into the capillary receiving opening of a bushing unit or a connecting unit and fixed in the bushing by means of a fastening screw which has a central bore for guiding the capillary. For sealing, one or more sealing elements which surround the capillary in the front end region thereof are pressed into the capillary receiving opening, which runs inward in a conical manner, by means of the fastening screw during the connection of capillary and bushing unit.

It is however a disadvantage here that the sealing action is provided not in the plane of the face surface, which is perpendicular to the longitudinal axis of the capillary, but rather is offset rearward from the face surface by a certain distance in an axial direction. This gives rise to a dead volume which has a disadvantageous effect in particular in the field of high-performance liquid chromatography. To be able to ensure the sealing action of such connections at the extremely high pressures used in high-performance liquid chromatography, use is often made of sealing elements such as are described as prior art for example in FIG. 2 of U.S. Pat. No. 4,619,473. These are sealing elements which are of annular cross section and which are normally likewise composed of high-grade steel and which, in longitudinal section, have a partially conical profile of the outer diameter. Here, the capillary projects with its foremost section through the sealing element into a cylindrical recess (pilot bore) in the bushing element. The bushing element widens conically proceeding from the rear end of the pilot bore, wherein the conical widening has a greater angle with respect to the longitudinal axis of the capillary than the sealing element. As a result, as the sealing element is pressed into the receiving opening by means of a fastening screw, an extremely high radially inwardly directed pressure is exerted on the front region of the sealing element, such that the sealing point is formed here. Said pressure however normally results in a deformation of the sealing element and of the capillary, wherein the sealing element is pressed by way of its front edge annularly into the outer circumference of the capillary.

Such a deformation is undesirable in particular because in this way, the sealing element is connected in a positively locking and non-positively locking manner to the capillary, and the sealing element can no longer be readily displaced in an axial direction on the capillary. If the sealing connection is released and if it is sought to screw a connector element of said type in to another bushing unit, for example because a component of the chromatography system must be replaced, then it is duly possible for a sealed connection to be produced again, but owing to tolerances or manufacturer-dependent differences in the depths of the receiving opening, it can no longer be ensured that the capillary, by way of its face surface, acts again on the face surface of the line to be connected. If the receiving opening of the bushing unit of the exchanged component is longer in an axial direction than in the case of the component used previously, an undesired dead volume is formed. If the receiving opening for the capillary in the exchanged component is shorter in an axial direction than in the case of the component used previously, the capillary is even deformed, possibly damaged, under the pressure of the fastening screw, and a sealed connection is no longer possible under some circumstances. This is because the sealing element that is fastened in a positively locking and non-positively locking manner to the capillary cannot move in an axial direction.

However, in the case of such a fitting, a certain dead volume is also scarcely avoidable if the face surfaces of the capillary and of the line to be connected are situated directly opposite or make contact, because the sealing point is situated not in the region of the face surface of the capillary or of the line to be connected.

To solve said problem, DE 10 2009 022 368 discloses a connector unit in which an annular sealing element is provided on the outer side of the capillaries. Said sealing element is inserted together with the capillary into the pilot bore of a bushing housing and has an axial thrust force exerted thereon such that, as a result of plastic or elastic deformation of the sealing element, sealing of the capillary connection is attained already in the region of the base surface of the pilot bore, whereby the formation of a dead volume is prevented. During the dismounting of the connection, the sealing element can also be pulled out of the pilot bore in a relatively simple manner together with the capillary.

Said connector unit is however disadvantageously suitable only for capillaries which, when inserted into the pilot bore, exhibit an adequate amount of space on the outer side of the capillary for the arrangement of the annular sealing element there. Since the above-described form of the bushing element of U.S. Pat. No. 4,619,473 has become established as a standard and, in the field of HPLC, a pilot bore diameter of approximately 1.7 mm has become established as a standard, the suitability of said plug-in connection is restricted to thin capillaries with outer diameters of considerably less than 1.7 mm, for example 200 μm to 500 μm, such as for example fused silica capillaries or else metal capillaries with an outer diameter of for example approximately 0.8 mm. The connector unit is however unsuitable for capillaries with larger outer diameters, such as for example the capillaries with approximately 1.6 mm outer diameter that are widely used in the field of HPLC.

SUMMARY

It was therefore an object of the invention to specify a connector unit compatible with the standardized bushing unit, which connector unit ensures a pressure-tight capillary connection for capillaries with a relatively large outer diameter which is approximately as large as the inner diameter of the pilot bore. It should also be possible for said capillaries to be reliably sealed off, in the region of their face side or within the pilot bore, with respect to high operating pressures. It was also an object to specify a plug-in connection, which can be easily mounted and dismounted, for such capillaries.

The invention is based on the realization that a sealing element used for sealing off a capillary connection can project at least partially into the interior of a capillary. The sealing element is thereby not only stabilized in terms of its position and subjected to a particularly uniform exertion of load, but it can thereby also be used in a particularly space-saving manner for connections in which the outer diameter of the capillary substantially corresponds to the inner diameter of a pilot bore into which the capillary is to be inserted for the purposes of connection. Finally, in this way, the sealing element can be connected to the capillary in a sufficiently firm manner such that, during dismounting, said sealing element can be pulled out of the pilot bore again together with the capillary, and does not for example remain stuck in said pilot bore.

Here, the connector unit according to the invention permits the axial exertion of thrust on the sealing element and the resulting plastic or elastic deformation thereof, which imparts a sealing action, directly in the region of the front face wall of the capillary. By contrast to the prior art, this is achieved even without a sealing element encircling the capillary on the outside.

An axial thrust force required for the deformation of the sealing element is in this case transmitted via the capillary to the sealing element. A separate axial exertion of force on the sealing element, as per the precedent of the prior art, on the outer side of the capillary can be advantageously dispensed with in principle. Thus, the connector unit according to the invention permits a particularly simple and at the same time pressure-tight connection of relatively thick capillaries. Said connector unit is in particular also suitable for high-performance liquid chromatography, because it permits sealing even with respect to the high operating pressures that are conventional in that field.

The connector unit comprises a connector housing with an axial bore. Here, a capillary running along a capillary axis projects through the axial bore of the connector housing. Furthermore, the connector unit comprises, at a foremost section of the capillary, a sealing element which is of preferably annular cross section and which is intended to impart the desired sealing action through elastic or plastic deformation. Here, the sealing action is generated within a pilot bore which belongs to a bushing unit that can be releasably connected to the connector housing. Here, in the connected state of the connector unit and bushing unit, the capillary projects into the pilot bore and is situated with its front end opposite, and substantially in alignment with, a bushing capillary or bushing capillary opening arranged in the bushing unit.

Here, according to the invention, the sealing element has a first section and a second section, wherein, at the foremost section of the capillary, the sealing element extends by way of its first sealing section into the interior of the capillary, such that the capillary surrounds the first sealing section in a targeted manner by way of a wall section situated radially further outward than the first sealing section.

Here, the second section of the sealing element projects beyond the front face side of the capillary by a distance and, during a displacement movement of the capillary in the direction of the opposite bushing unit, has exerted thereon a thrust force which deforms the second sealing section. Here, the second sealing section lies against the contours of the adjacent elements or wall surfaces and seals off existing gaps without thereby closing off the face-side opening of the capillary and the passage into the opposite bushing capillary or bushing capillary opening.

By virtue of the fact that the first sealing section extends into the interior of the capillary, an axial thrust force introduced into the wall of the capillary can be transmitted in a highly effective manner to the sealing element that projects into the capillary, such that the thrust force ultimately leads to the desired sealing action through deformation of the second sealing section which adjoins the first sealing section and which projects forward out of the capillary. At the same time, the sealing element can be mounted in a particularly simple manner in that, in the dismounted state (connector unit is separated from the bushing unit), said sealing element is inserted by way of its first sealing section into the capillary at the face side and is then inserted together with said capillary into the pilot bore of the bushing unit.

In one expedient embodiment of the invention, the first sealing section is in the form of a hollow cylinder which projects into the capillary concentrically with respect to the capillary axis. Here, the first sealing section can bear by way of its outer shell surface against an inner surface, of complementary shape thereto, of the capillary, whereby the sealing element is stabilized in terms of its position in a highly effective manner. The cylindrical contact surface between the first sealing section and the capillary is furthermore highly suitable for the transmission of the thrust force from the capillary to the sealing element, in the form of a shear stress along said surface.

As stated above, one expedient embodiment of the invention provides that, in the non-connected state, the sealing element projects by way of its second sealing section beyond the front end of the capillary (the expression "front" should be understood hereinafter to mean a position facing toward the bushing unit or situated at the free end of the capillary or of the sealing element). Here, the second sealing section can advantageously deform under the exertion of thrust such that the face-side end of the capillary extends to a point as close as possible to the base of the pilot bore, and the dead volume in the region of the front capillary end and of the opposite bushing capillary is as small as possible. Through suitable shaping of the second sealing section that projects forward beyond the capillary, it can be ensured here that the deformation of said second sealing section under the exertion of thrust loading takes place preferentially in an axial or radially outward direction. A radially inward deformation could influence the free flow cross section of the capillary, and should be avoided.

According to the invention, that region of the capillary into which the first sealing section projects may be shaped in different ways. What is firstly conceivable is an annular chamber formed within the wall of the capillary and concentrically with respect to the capillary axis, it being possible for said annular chamber to be filled out by the first sealing section by way of a hollow cylinder shape complementary to the annular chamber. Said variant ensures particularly secure purchase of the sealing element as a result of contact with the capillary both on the inside and also on the outside of the first sealing section.

By contrast, a further particularly expedient variant provides for the first sealing section to be arranged in a cylindrical recess concentric with respect to the capillary axis. So as not to impede the free flow cross section of the capillary, said recess may in particular be a bore which widens the flow cross section in the front capillary end, wherein the first sealing section, by way of its annular form in cross section, fills out the resulting additional capillary volume so as to form a substantially unchanged continuation of the original flow cross section of the capillary as far as the front (second) section of the sealing element. Such a bore which widens the capillary is easy to produce and can be readily adapted in a precise manner to the outer diameter of the first sealing section to be used.

A cylindrical recess or bore in the front end of the capillary also permits the implementation of a further advantageous embodiment of the invention in which the sealing element is supported or stabilized at its inner side. Said embodiment corresponds to the variant mentioned above, wherein it is however the case that the inner bore of the substantially hollow cylindrical sealing element has inserted into it a further, likewise substantially hollow cylindrical insert element. Said insert element is composed of a significantly harder material than the sealing element, and prevents inadmissible deformation of the sealing element in said region under the exerted thrust force.

Said insert element firstly permits stabilization of the first sealing section from the inside, such that said sealing section is supported at the inside by the outer shell surface of the insert element and at the outside by the wall of the drilled-out capillary. Furthermore, what has proven to be particularly effective is a variant in which the insert element engages behind the first sealing section in an axial direction in order to achieve a positively locking transmission of force from the capillary via the insert element to the sealing element. Here, the insert element has an inner diameter which runs concentrically with respect to the capillary axis and which substantially corresponds to that of the free flow cross section of the capillary. Thus, the inner diameter of the capillary is in turn continued as far as the front end, and a narrowing of the effective flow cross section is avoided.

The insert element provided for stabilization and advantageous exertion of thrust on the first sealing section is expediently in the form of a sleeve which, at its rear end facing away from the front capillary end, has a flange-like widened portion. The outer diameter of said flange-like widened portion preferably corresponds here to that of the bore by way of which the capillary has been widened. At the same time, said outer diameter corresponds to the outer diameter of the first, annular sealing section. Correspondingly, the first sealing section bears, by way of its rear end, against the flange-like widened portion of the insert element, and can be subjected via said end to a forwardly directed thrust force. The insert element itself is supported, at its rear end (the rear side of the flange-like widened portion), on the annular section of the capillary formed by the bore described above.

The insert element according to the invention (which can also be referred to as an inlay) supports the first sealing section against inward radial deformation in an effective manner, such that an undesired deformation of the first sealing section is not possible. For this purpose, the insert element may for example be formed from high-grade steel, titanium or a titanium-containing material in order to satisfy the particularly high requirements with regard to the strength and chemical resistance in the field of high-performance liquid chromatography.

A further advantageous embodiment of the connector unit provides that the entire capillary is lined on the inside with a lining, which is composed in particular of a plastics material. The plastics linings may be formed as an inner coating of the capillary or as a tubular element to be inserted separately into the capillary. In the case of such a capillary known per se and the associated connector unit according to the invention, the liquid conducted through does not come into contact with metal at any point, which is advantageous for certain HPLC applications. Such a lined capillary is free from metal on the inside and, by contrast to plastics capillaries, for example, can withstand high pressures because the outer capillary acts as a supporting corset and increases the strength of the capillary as a whole.

In a further advantageous embodiment of the invention, the first sealing section may be formed as part of or connected integrally to the plastics lining.

In this case, the first sealing section projects into the capillary at the face side and extends in tubular form within the capillary over the entire length of the capillary. The second sealing section which projects forward out of the capillary may in this case be formed by thermal deformation of a free end of the plastics lining inserted into the capillary, whereby a fixed connection is produced between the second sealing section outside the capillary and the first sealing section within the capillary, which is at the same time the plastics lining. Here, the sealing element, at least at its second sealing section, exhibits sufficient plastic deformability in order to be able to realize the desired sealing action under the exertion of thrust.

An alternative embodiment provides a plastics lining of the capillary also for the arrangement in which the first sealing section is radially supported, and/or can have axial load exerted thereon, on its inner side by the above-described insert element, such that the support tube in the front capillary region lines the inside of and stabilizes the insert element and, adjoining the latter axially to the rear, the capillary. Then, from the inside to the outside, the free flow cross section of the capillary is adjoined by the support tube, the latter adjoins the insert element, the insert element adjoins the first sealing section, and said first sealing section adjoins the inner wall of the widened capillary which surrounds the aforementioned elements. Such an arrangement makes it possible in a small space to form a sealed, high-strength and chemical-resistant capillary connection, with simultaneous axial exertion of thrust on and radial stabilization of the first sealing section.

In the non-connected or else in the connected state of the connector unit and bushing unit, the second sealing section which projects out of the capillary at the face side may be widened in a radial direction for example as far as the outer diameter of the capillary or the inner diameter of the pilot bore. It is thus ensured that the capillary with inserted sealing element fills out the volume of the pilot bore as completely as possible, and avoids the formation of a dead volume, already during the manual insertion thereof into the pilot bore. Thus, the subsequent exertion of thrust on the second sealing section has the direct result that said second sealing section lies or presses against that wall of the pilot bore which is adjacent at the face side or radially, without it firstly being necessary here for dead spaces to be filled out. By means of a relatively short axial displacement travel of the capillary with the sealing element inserted at the front, it is thus possible to attain a particularly good sealing action.

That face side of the capillary which preferably directly adjoins the second sealing section may extend radially outward for example at right angles to the capillary axis. To attain a preferred deformation behavior of the second sealing section, the face side of the capillary may however also follow a profile which is formed by a straight line inclined with respect to the capillary axis or by a sweeping curve. In this way, the deformation of the second sealing action under exertion of thrust may be directed, for example in order to achieve a preferentially radially outwardly directed movement of material. It is basically possible to provide any profile shape which promotes abutment of the sealing element against the pilot bore, or else against the face surface of the capillary, with particularly effective sealing action.

To make it possible for an axial thrust force to be imparted to the sealing element or to the second sealing section thereof in a particularly effective manner, one advantageous development of the connector unit provides that a preferably hollow cylindrical thrust piece is provided which engages around the capillary from the outside. The thrust piece is fixedly connected to the capillary such that an axial thrust force can be transmitted from the thrust piece to the capillary without a relative movement between the thrust piece and capillary taking place. The rear face side of the thrust piece is expediently formed such that, in the connected state of the connector unit and bushing unit, said rear face side can have an axial thrust force exerted thereon by the connector housing. As a result of said exertion of load, the thrust piece together with the capillary and the sealing element seated therein are pushed axially forward in the direction of the bushing unit, whereby the second sealing section undergoes a plastic or elastic deformation, which provides a sealing action in any case.

The fixed connection between the thrust piece and capillary may be realized by means of frictional locking, positive locking or else a combination of both. Cohesive connection types, such as for example welding, soldering or adhesive bonding, may also be used. The thrust piece can be connected to the capillary in a relatively simple manner in particular by means of crimping.

Here, one advantageous development provides that the thrust piece and the first sealing section projecting into the capillary at least partially overlap, or are at least partially superposed, in an axial direction. In this case, the thrust piece engages over the capillary and at least partially also over the first sealing section arranged therein. By means of a crimped connection, it is the case in said common overlap region that not only the thrust piece is connected to the capillary but—depending on the type and strength of the crimped connection—said capillary is also connected to the first sealing section arranged at the inside. Here, a particularly stable connection is obtained if, on its inner side, the first sealing section is in turn supported radially by the above-described insert element.

BRIEF DESCRIPTION OF THE DRAWINGS

Some embodiments of the invention will be explained in more detail below on the basis of figures, in which.

DETAILED DESCRIPTION OF EMBODIMENTS

Figure 1:
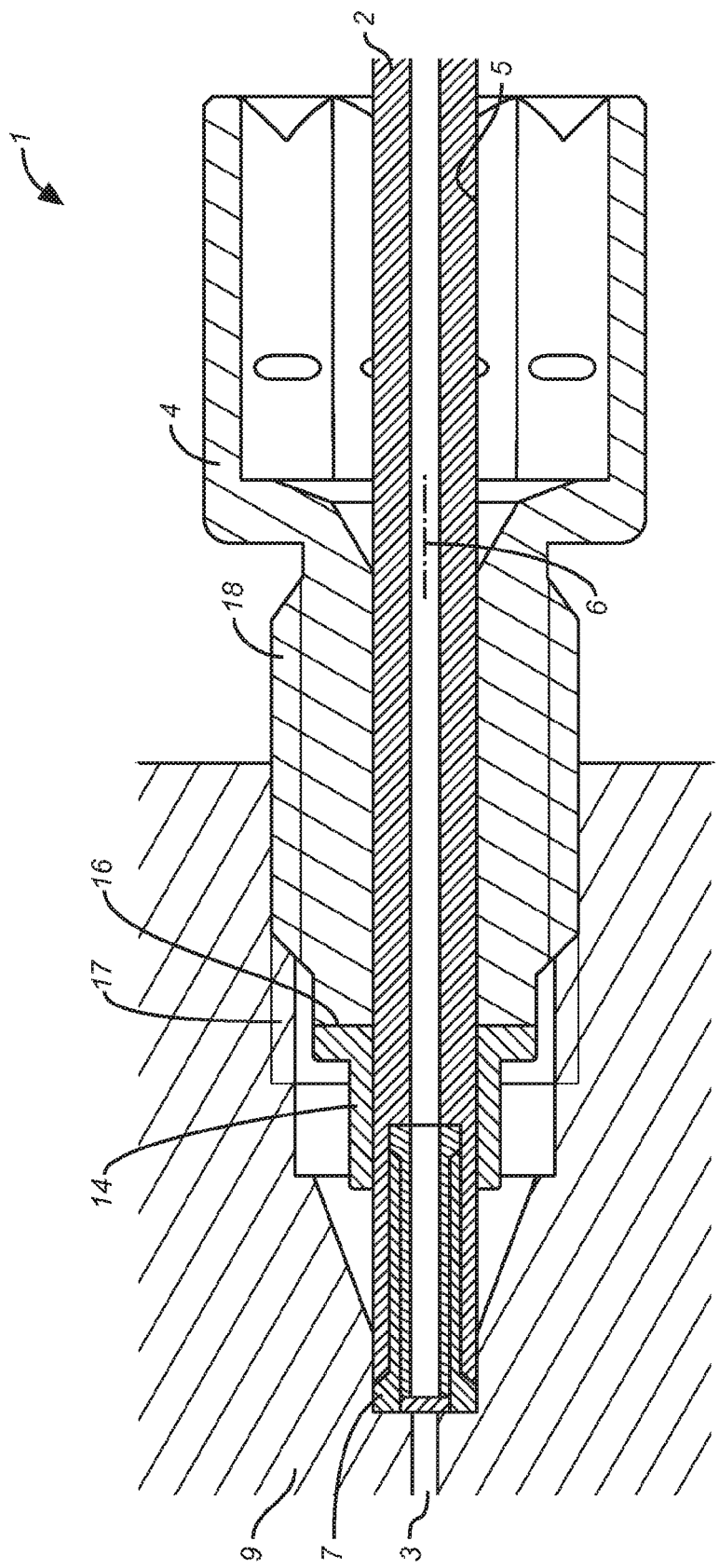
FIG. 1 shows a first embodiment of a plug-in connection with insert element.

The arrangement shown in FIG. 1 exhibits a connector unit 1, it being the intention for said connector unit to be connectable to a bushing unit 9. Here, the connector unit 1 comprises a connector housing 4 which has a central axial bore 5. The connector housing 4 is provided with an external thread 18 which can be screwed into a matching internal thread 17 of the bushing unit 9, whereby the connector unit 1 moves forward (to the left in FIG. 1) toward the bushing unit 9 by a distance.

In the bore 5 of the connector housing 4 there is arranged a capillary 2 which projects all the way through the connector housing 4 along a capillary axis 6. The capillary 2 is situated with its front or face end opposite, and substantially in alignment with, a bushing capillary 3 within the bushing unit 9. A thrust piece 14 which can have a thrust force exerted thereon in an axial direction via a rear-side abutment surface 16 by the connector housing 4 surrounds and is fixedly connected to the capillary 2. By virtue of the connector housing 4 being screwed into the internal thread 17, the thrust piece 14, and with it the capillary 2 fixedly connected thereto, are moved forward in order to connect the capillary 2 to the bushing capillary 3 with a sealed plug-in connection.

Figure 2:
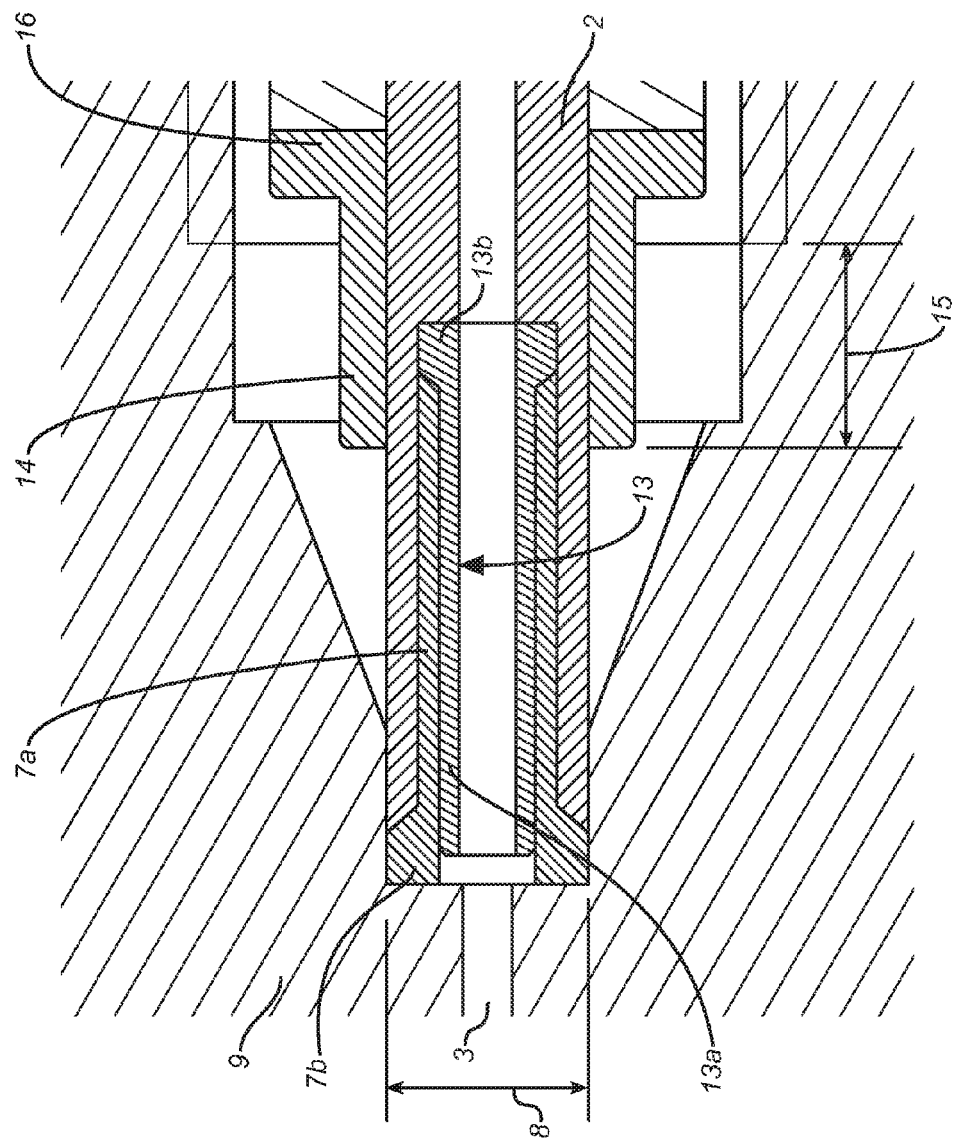
FIG. 2 shows a detail view of the embodiment as per FIG. 1.

The detail view illustrated in FIG. 2 shows the front section of the capillary 2 which projects as far as into a pilot bore 8 which is formed into the bushing unit 9 substantially concentrically with respect to the bushing capillary 3. Whereas the outer diameter of the capillary 2 substantially corresponds to the inner diameter of the pilot bore 8, the inner diameter of the capillary 2 is enlarged by a bore formed in on the inside and concentrically with respect to the capillary axis 6. A sealing element 7 composed of a first sealing section 7a and of a second sealing section 7b projects by way of the first, hollow cylindrical sealing section 7a into said widened recess of the capillary 2 at the face side. Here, an insert element 13 arranged within the first sealing section 7a supports the first sealing section 7a radially to the inside by way of a front section 13a. In FIG. 2, the inner diameter of the insert element 13 substantially corresponds to the original inner diameter of the capillary 2 as can be seen in the right-hand part of FIG. 2. This has the advantage that the flow cross section in the connector unit is not constricted, though this is not imperatively necessary. For example, in the case of capillaries with a very large inner diameter, it may be necessary for the insert element to have a smaller inner diameter than the capillary. Likewise, for manufacturing reasons, a standardization of the insert element inner diameter may be expedient.

The insert element 13 engages behind the first sealing section 7a by way of a flange-like widened portion 13b which, on the rear end of the first sealing section 7a, extends radially outward as far as the widened inner diameter of the capillary 2, whereby the flange-like widened portion 13b firstly is connected in a positively locking manner to the capillary 2 and thus can have a thrust force exerted thereon by the capillary 2, and secondly can in turn transmit the thrust force in a positively locking manner to the sealing section 7a in an axial direction.

The second sealing section 7b adjoining the first sealing section 7a projects in an axial direction beyond the face side of the capillary 2, wherein the diameter of said second sealing section widens to approximately the inner diameter of the pilot bore 8. The insert element 13 also projects within the sealing element 7 axially beyond the face side of the capillary 2, but not as far as the second sealing section 7b.

The thrust piece 14 engages around the outer shell surface of the capillary 2 along an axial region 15 of said capillary and is—as described—fixedly connected to the capillary 2. The thrust piece 14, which bears by way of its rear abutment 16 against the connector housing 4, pushes the capillary 2 with the sealing element 7 inserted therein and with the insert element 13 into the pilot bore 8 of the bushing unit 9 during a screwing-in movement of the connector housing 4 into the bushing unit 9. During said forward movement, the second sealing section 7b, which extends further forward (to the left in FIG. 2) in an axial direction than the capillary 2 and the insert element 13, is pressed against the base of the pilot bore 8 by means of the capillary 2 and/or the insert element 13, and is forced to undergo a plastic and/or elastic deformation. Here, the front sealing section 7b lies closely against the surrounding components or boundary surfaces, such that a medium to be conveyed through the capillary 2 is prevented from escaping to the outside of the capillary 2.

Here, since the capillary 2 projects into the pilot bore 8, said capillary is radially supported on its outer side by the bore wall, and is thus held in a particularly stable manner.

During the course of the forward movement, the face side of the capillary 2 and of the insert element 13 may move slightly further toward the base of the pilot bore 8, but without abutting against said base. The axial projecting length of the insert element may furthermore be selected so as to block an expansion of the second sealing section radially inward, such that the inner diameter of the capillary connection is not constricted.

Figure 3:
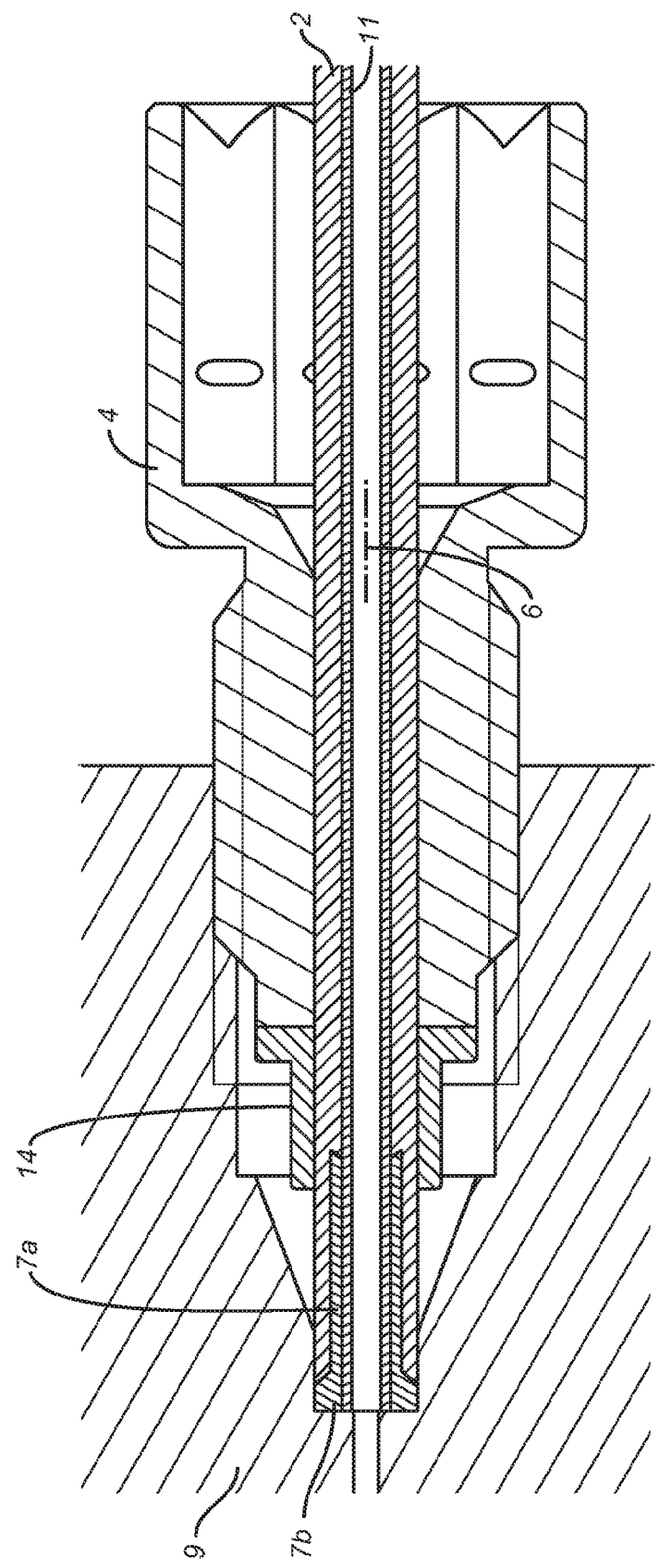
FIG. 3 shows a modified variant with plastics lining on the inside.

FIG. 3 shows a modified embodiment as per FIG. 2. Here, the insert element 13 is omitted, such that the first sealing section 7a extends in a radially inward direction as far as the original diameter of the capillary 2. However, the first and second sealing sections 7a, 7b are, like the capillary 2 as a whole, provided on the inside with a plastics lining 11 which protects the capillary 2 against direct contact with a medium. The thrust force for the actuation of the second sealing section 7b is in this case transmitted from the capillary 2 directly to the first sealing section 7a. This may take place at the rear end of the first sealing section 7a by means of positive locking with the shoulder of the capillary 2 formed as a result of the widening of the foremost capillary section. A transmission of the thrust force as a shear stress via the cylindrical contact surface between the capillary 2 and first sealing section 7a is also possible.

Figure 4:
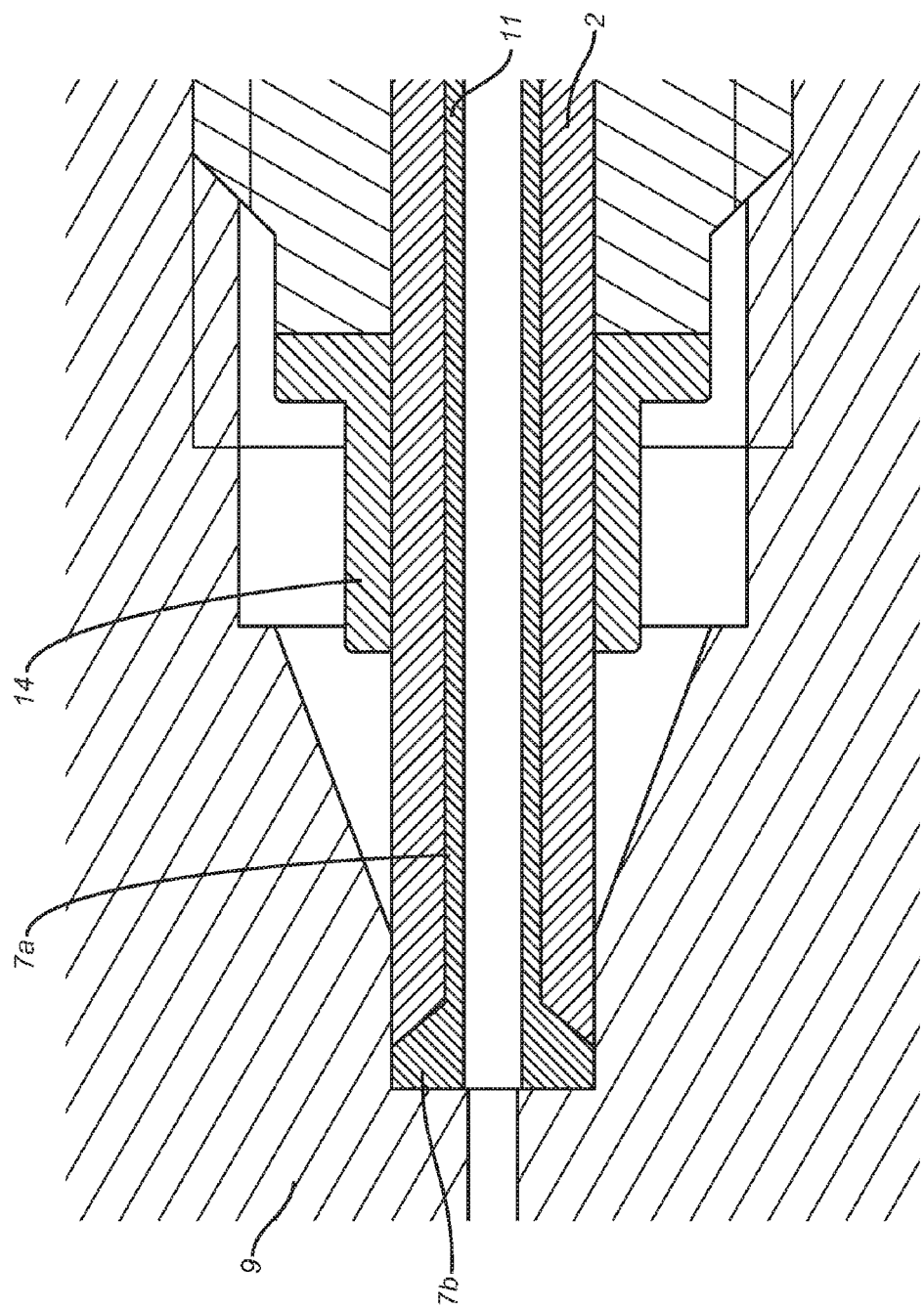
FIG. 4 shows a sealing element formed integrally with the plastics lining.

The enlarged view as per FIG. 4 shows a further variant in which the sealing element 7 is formed in one piece with the inner plastics lining 11 of the capillary, such that the second sealing section 7b merges into the first sealing section 7a which extends into the capillary 2 at the face side, which first sealing section simultaneously constitutes the plastics lining 11. In this embodiment, there is no need for a widened bore or recess in the front section of the capillary. Instead, the thrust force to be transmitted to the second sealing section 7 is transmitted as a shear stress via the cylindrical contact surface between the capillary 2 and the first sealing section 7a and by means of positive locking in the region of the radial widened portion of the second sealing section 7b adjacent to the face side of the capillary 2.

Figure 5:
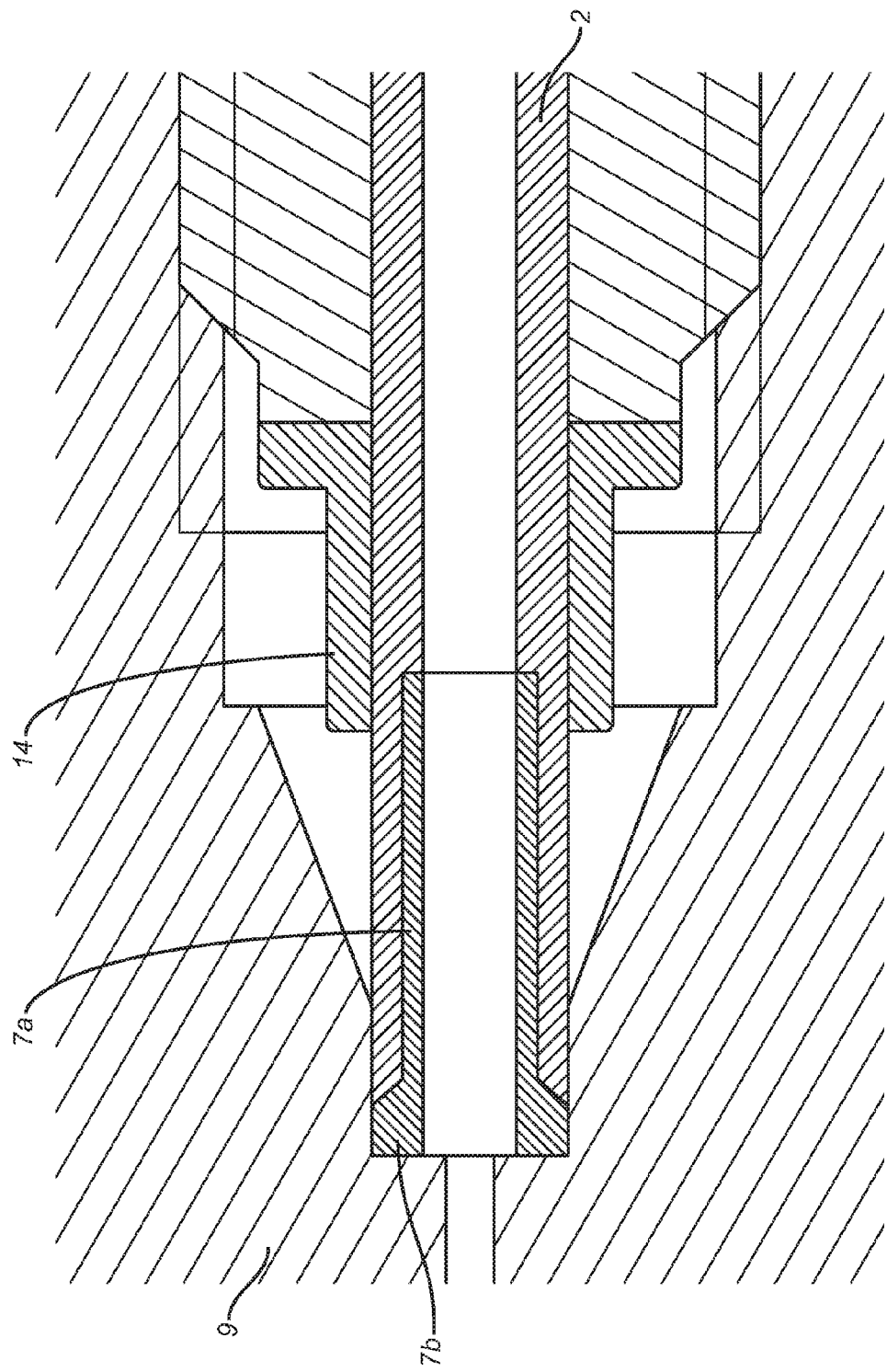
FIG. 5 shows a simple variant with a sealing element without insert element.

FIG. 5 shows a variant which is simplified in relation to FIG. 1. Here, too, the capillary 2 has been widened at its front end by means of a bore into which the first sealing section 7a of the sealing element 7 has been inserted. Here, the inner diameter of the sealing element substantially corresponds to the free diameter of the capillary behind the widened bore. An insert element has been omitted here. Here, too, the thrust piece 14 fastened to the capillary 2 from the outside again makes it possible for an axial thrust force to be exerted on the capillary 2, which axial thrust force acts on the sealing element, and in particular on the second section 7b thereof, in the front region of the capillary 2.

Figure 6:
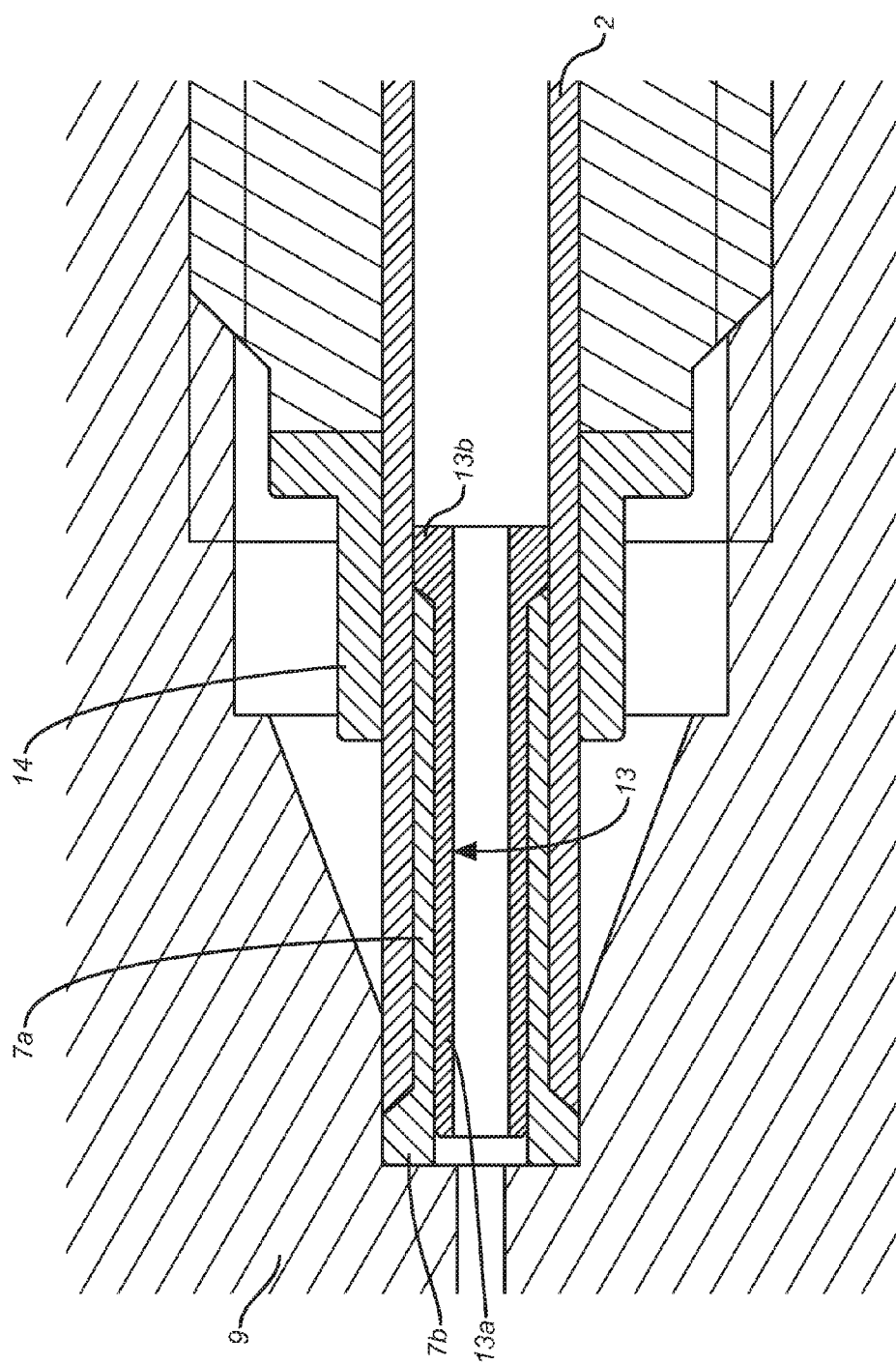
FIG. 6 shows a variant with a sealing element and insert element in a non-widened capillary.

The variant as per FIG. 6 shows the situation in which the capillary 2 is formed without a widening of its inner diameter at its front end. Correspondingly, the first sealing section 7a extends into the capillary along the unmachined inner wall of said capillary. Similarly to the embodiment as per FIGS. 1 and 2, it is the case here, too, that the first sealing section 7a of the sealing element is again stabilized from the inside by an insert element 13, wherein the insert element 13 extends by way of a first section 13a along the inner wall of the first sealing section 7a and supports said first sealing section in a positively locking manner by way of a flange-like widened portion 13b on the rear end. The sealing element 7 and insert element 13 constrict the free cross section of the capillary 2.

The insert element 13 situated at the inside permits a particularly effective crimped connection between the thrust piece 14 and the capillary 2, for which purpose the insert element 13 extends in an axial direction at least partially into the region superposed, on the outer side of the capillary 2, by the thrust piece 14.

Figure 7:
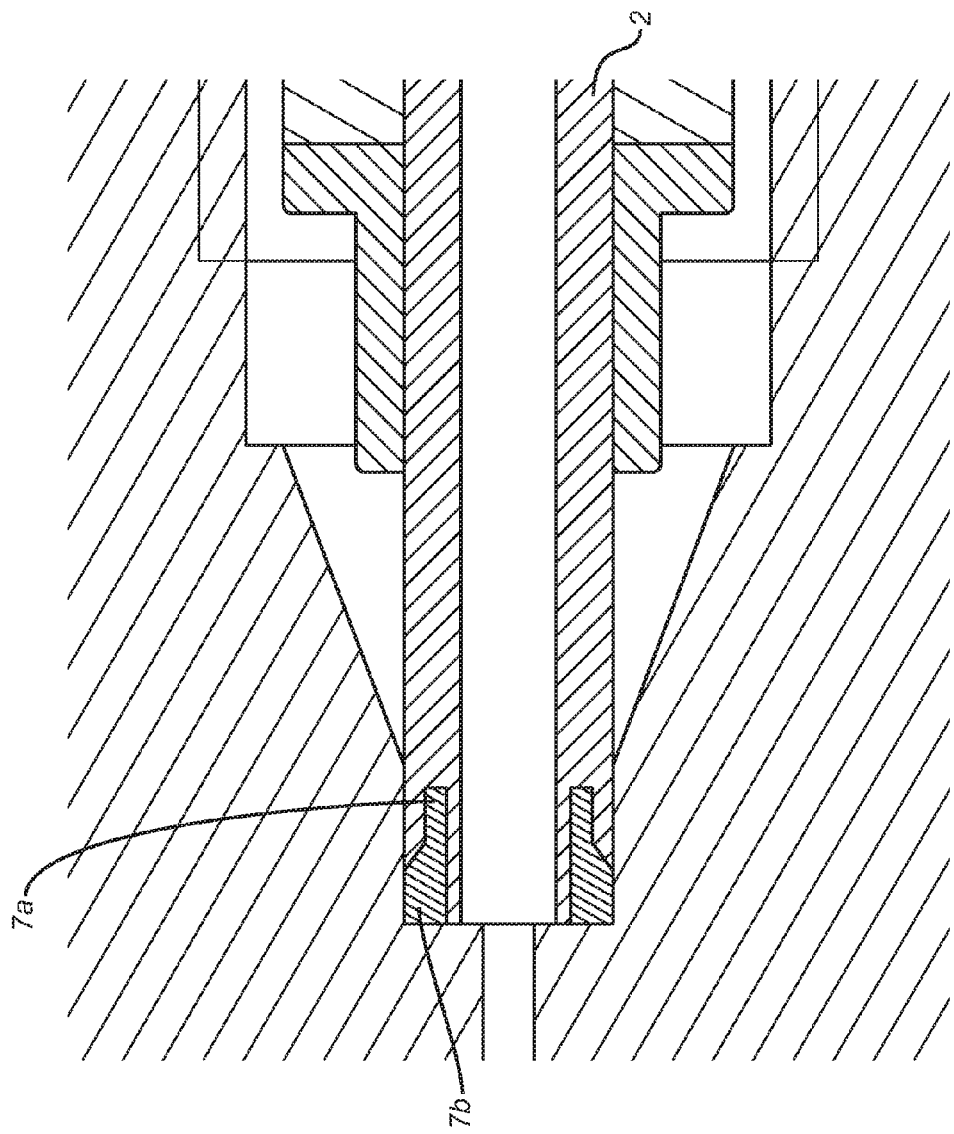
FIG. 7 shows a variant with an annular receptacle within the wall of the capillary.

Finally, FIG. 7 shows a further embodiment of the invention in which the first sealing section projects into a recess formed annularly into the face side of the capillary 2. Here, the first sealing section 7a is supported both on its inner side and on its outer side in a radial direction by the capillary 2, wherein the second sealing section 7b which adjoins the first sealing section 7a projects beyond the capillary 2 in an axial direction and, in so doing, widens radially as far as the outer diameter of the pilot bore 8, which is not shown in any more detail in FIG. 5. Although the production of the annular-chamber-like recess in the face side of the capillary 2 is technically more cumbersome, the sealing element 7 can be received and guided, and pressed with positive locking action against the base and the side wall of the pilot bore 8 in order to attain the desired sealing action, in an effective manner without additional auxiliary means.

It is self-evidently possible for individual features of embodiments explained above only in conjunction with the respective figure to also be combined to form further embodiments which are not illustrated, wherein said further embodiments likewise have the stated advantages.

The invention claimed is:
1. A connector unit for connecting capillaries comprising:
a) a connector housing which has an axial bore,
b) a capillary which runs along a capillary axis and which has an inner diameter and which projects through the axial bore of the connector housing,
c) a sealing element,
d) a front end of the capillary is sealed off with an elastic and/or plastic deformation of the sealing element with respect to a pilot bore of a bushing unit which is releasably connected to the connector housing,
e) wherein, in a connected state of the connector unit and the bushing unit, the capillary projects into the pilot bore and is situated with the front end opposite, and substantially in alignment with, a bushing capillary or a bushing capillary opening of the bushing unit,
f) wherein the sealing element has a first sealing section and a second sealing section, wherein, at a foremost section of the capillary, the first sealing section extends into an interior of the capillary, and
g) a section of an insert element is arranged within the first sealing section to support the first sealing section in a radial direction.

2. The connector unit as in claim 1, in that the first sealing section has a form of a hollow cylinder running concentrically with respect to the capillary axis.

3. The connector unit as in claim 1, in that, in a non-connected state of the connector unit and the bushing unit, the second sealing section of the sealing element projects facing away from the bushing unit and beyond a front end of the capillary.

4. The connector unit as in claim 1, in that the first sealing section projects into a recess provided on a face side in the capillary, the recess having
 a) an annular chamber within a wall of the capillary, or
 b) a cylindrical shape concentric with respect to the capillary axis.

5. The connector unit as in claim 1, in that the insert element engages behind the first sealing section to exert a forwardly directed thrust force.

6. The connector unit as in claim 1, in that the insert element extends radially outward as far as the inner diameter of the capillary.

7. The connector unit as in claim 1, in that the insert element is in a form of a sleeve, a rear end of the sleeve, facing away from the front capillary end, has a flange-like widened portion, the flange-like widened portion exerts a forwardly directed thrust force on the first sealing section.

8. The connector unit as in claim 1, in that an entire inside of the capillary is lined with a plastic lining.

9. The connector unit as in claim 8, in that the first sealing section is connected integrally to the plastic lining.

10. The connector unit as in claim 1, in that the sealing element widens radially from the first sealing section towards the second sealing section, wherein in a non-connected state of the connector unit and bushing unit, an outer diameter of the second sealing section substantially corresponds to an outer diameter of the capillary.

11. The connector unit as in claim 10, in that a front face wall of the capillary is shaped in a manner complementary to a transition profile of the sealing element from the first sealing section to the second sealing section.

12. The connector unit as in claim 1, in that in a non-connected state of the connector unit and bushing unit, an outer diameter of the second sealing section substantially corresponds to an inner diameter of the pilot bore.

13. The connector unit as claimed in claim 1 further comprising:
 a) a hollow cylindrical thrust piece which engages around the capillary in an axial region facing away from a front face surface of the capillary, and
 b) in that the thrust piece has a rear face side which faces away from a front end of the capillary and which, in the connected state of the connector unit and bushing unit, has an axial thrust force exerted thereon by the connector housing,
 c) wherein the thrust piece is fixedly connected to the capillary such that an axial thrust force can be transmitted to the capillary without a relative movement between the capillary and the thrust piece.

14. The connector unit as in claim 13, in that the thrust piece and the first sealing section at least partially overlap in an axial direction.

15. The connector unit as in claim 13, in that the thrust piece and the capillary are fixedly connected with a frictional lock and/or a positive lock.

16. A connection system for connecting a capillary and a bushing capillary comprising:
 a bushing unit; and
 a connector unit of claim 1 releasably connected to the bushing unit, wherein the bushing unit has the pilot bore into which the capillary extends when the connector unit and bushing unit are in a connected state, and wherein an inner diameter of the pilot bore substantially corresponds to an outer diameter of the capillary.

17. The connector unit as in claim 1, in which the sealing element has an annular cross section.

18. The connector unit as in claim 7, in which the flange-like widened portion has an outer diameter that corresponds to an outer diameter of the first sealing section.

19. The connector unit as in claim 8, in which the plastic lining extends forward as far as a face side of the capillary.

20. The connector unit as in claim 8, in which the plastic lining extends forward as far as a face side of the second sealing section.

21. The connector unit as in claim 15, in which the positive lock comprises a crimped connection.

* * * * *